(12) United States Patent
Wolters et al.

(10) Patent No.: US 10,123,810 B2
(45) Date of Patent: Nov. 13, 2018

(54) MEDICAL INSTRUMENT SET AND METHOD OF USE FOR TREATING BONY ABERRATIONS OF THE CALCANEUS

(71) Applicant: Life Spine, Inc., Huntley, IL (US)

(72) Inventors: Madeline C. Wolters, Carol Stream, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 257 days.

(21) Appl. No.: 15/249,420

(22) Filed: Aug. 28, 2016

(65) Prior Publication Data

US 2017/0056029 A1 Mar. 2, 2017

Related U.S. Application Data

(60) Provisional application No. 62/213,364, filed on Sep. 2, 2015.

(51) Int. Cl.
*A61B 17/16* (2006.01)
*A61B 17/17* (2006.01)
(Continued)

(52) U.S. Cl.
CPC ...... *A61B 17/1682* (2013.01); *A61B 17/1604* (2013.01); *A61B 17/1739* (2013.01);
(Continued)

(58) Field of Classification Search
CPC ............ A61B 17/1682; A61B 17/8822; A61B 17/1739
See application file for complete search history.

(56) References Cited

U.S. PATENT DOCUMENTS 3,017,887 A * 1/1962 Heyer ................ A61B 17/1739
128/DIG. 26
3,112,743 A * 12/1963 Di Cosola .......... A61B 17/1622
606/80

(Continued)

FOREIGN PATENT DOCUMENTS

WO    WO 2013/006663    1/2013

OTHER PUBLICATIONS

Search Report and Written Opinion for International Application No. PCT/US2016/049866, dated Jan. 24, 2017, 15 pages.

*Primary Examiner* — Christian Sevilla
(74) *Attorney, Agent, or Firm* — Foley & Lardner LLP

(57) ABSTRACT

A medical instrument set and method of use for surgically treating bony aberrations of the calcaneus such as calcaneal compression fractures. The present medical instrument set allows surgical treatment of bony aberrations through a minimally invasive procedure that provides better outcomes than both a closed reduction and an open reduction procedure. The medical instrument set includes one or more of an access needle, drill, depth guide, cement plunger, and curette. The access needle is used to provide access to a desired calcaneal site and is characterized by a cannula and a removable trocar tip. The drill is used to bore into the calcaneus. The depth guide is used to visually indicate how far a medical instrument extends beyond and/or through the access needle cannula. The cement plunger is used to introduce bone cement into the desired calcaneal site. The curette is used to mechanically create a void at the desired calcaneal site.

18 Claims, 11 Drawing Sheets

(51) Int. Cl.
*A61B 17/88* (2006.01)
*A61B 17/34* (2006.01)
*A61B 90/00* (2016.01)

(52) U.S. Cl.
CPC ...... *A61B 17/3472* (2013.01); *A61B 17/8805* (2013.01); *A61B 17/8822* (2013.01); *A61B 2090/062* (2016.02)

(56) References Cited

U.S. PATENT DOCUMENTS

| | | | |
|---|---|---|---|
| 6,575,919 B1* | 6/2003 | Reiley | A61B 17/34 600/567 |
| 2005/0165404 A1 | 7/2005 | Miller | |
| 2007/0066987 A1* | 3/2007 | Scanlan, Jr. | A61B 10/025 606/184 |
| 2008/0119821 A1* | 5/2008 | Agnihotri | A61B 10/025 604/513 |
| 2010/0145340 A1* | 6/2010 | Phan | A61B 17/3417 606/79 |

* cited by examiner

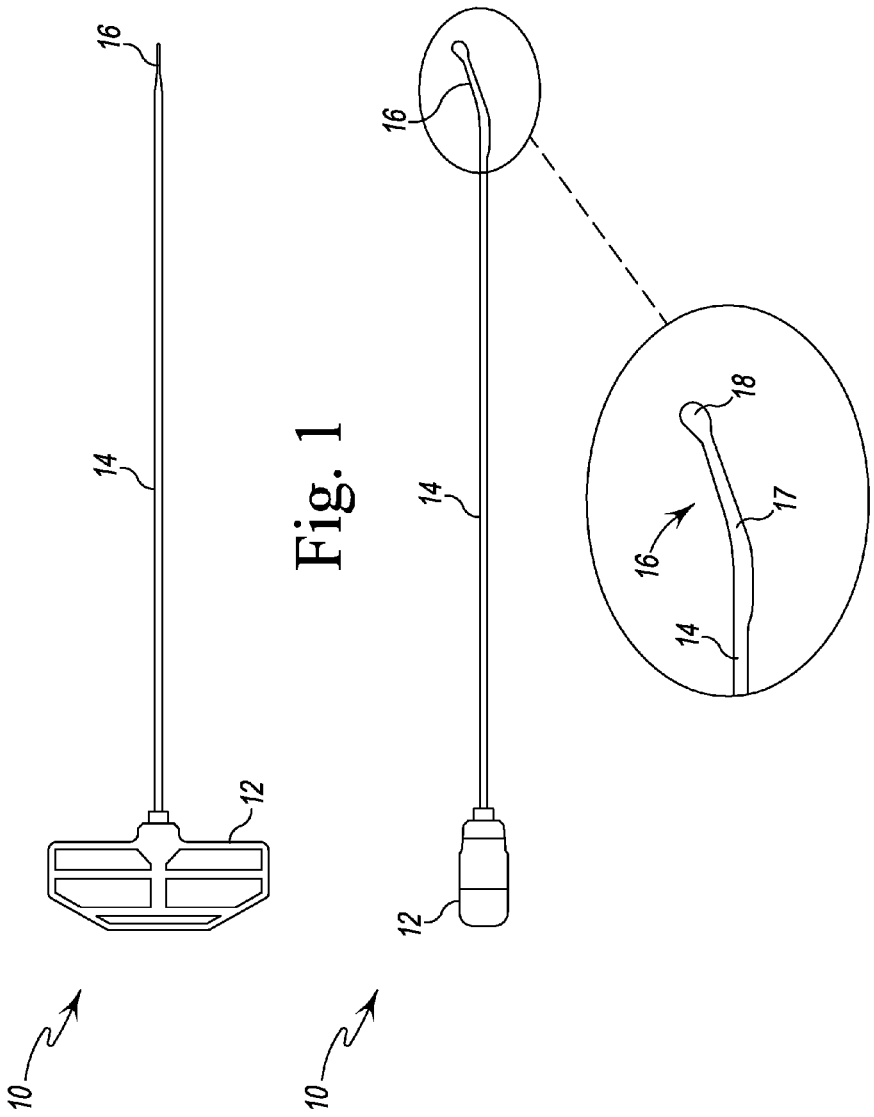

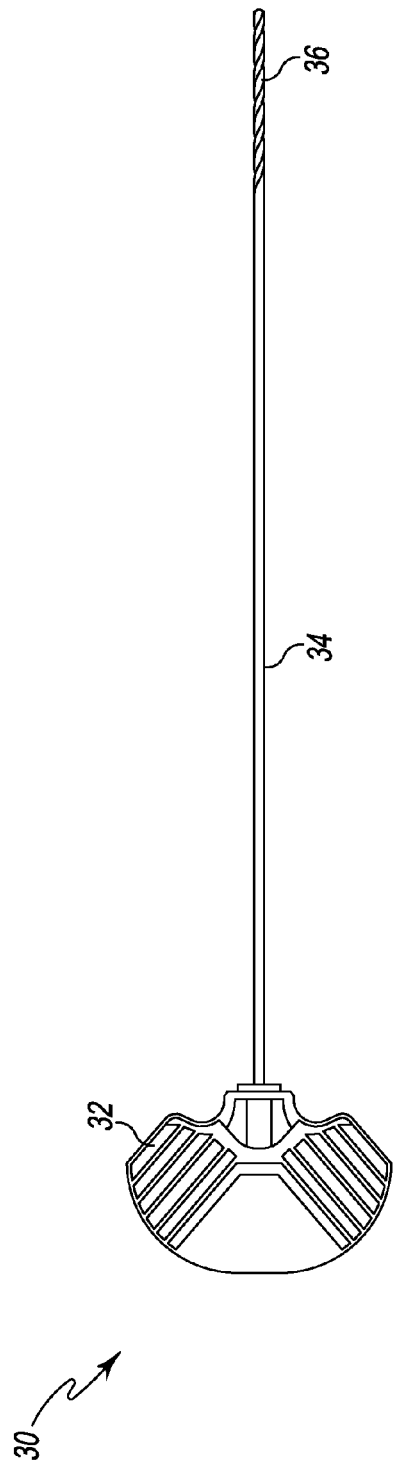
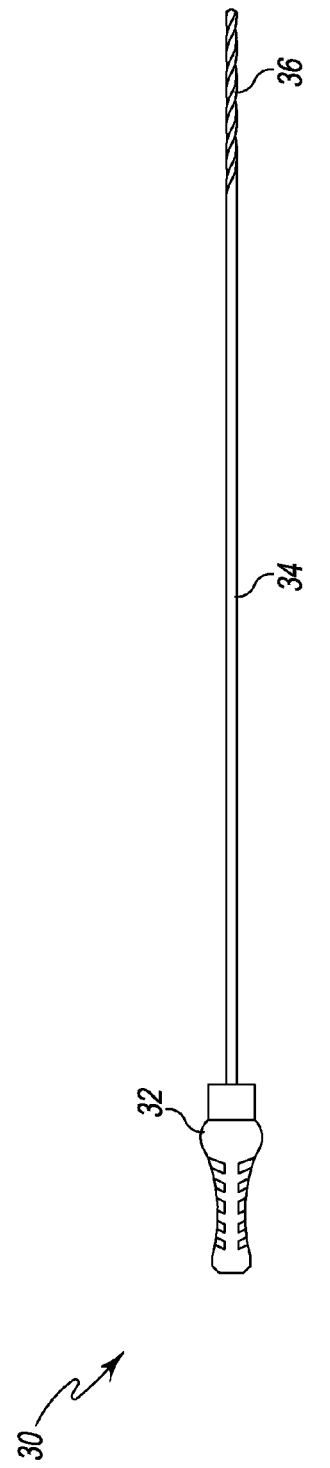
Fig. 5
Fig. 6

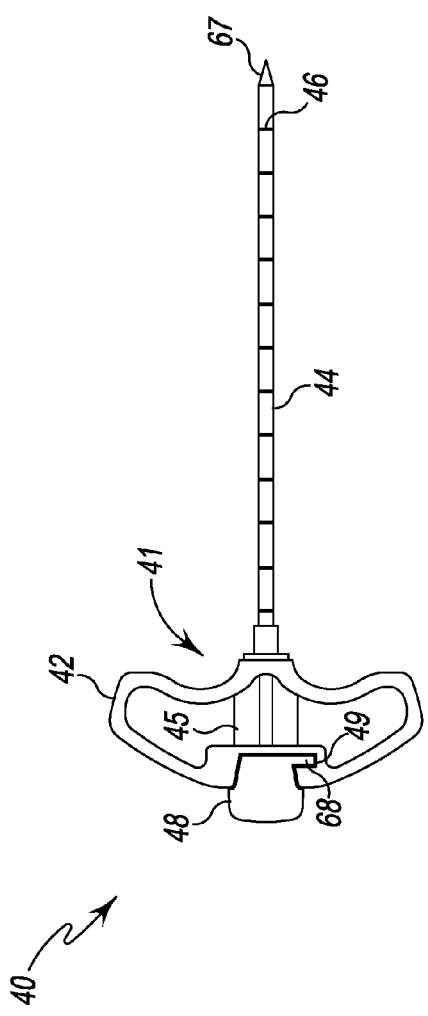
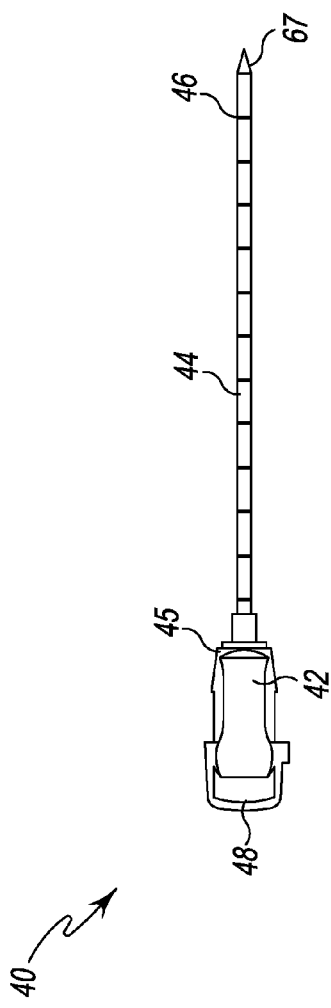
Fig. 7
Fig. 8

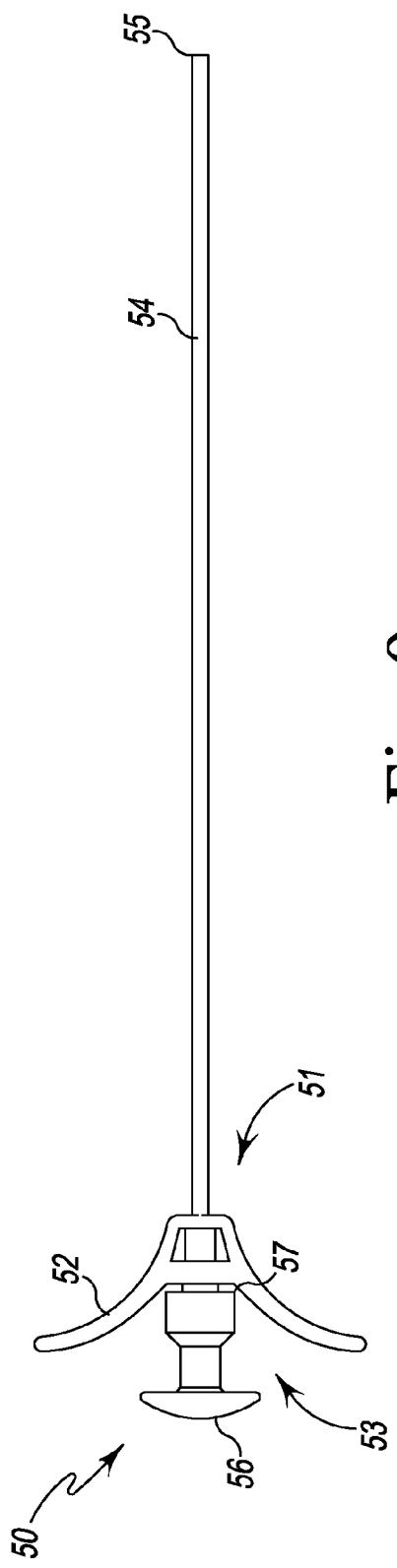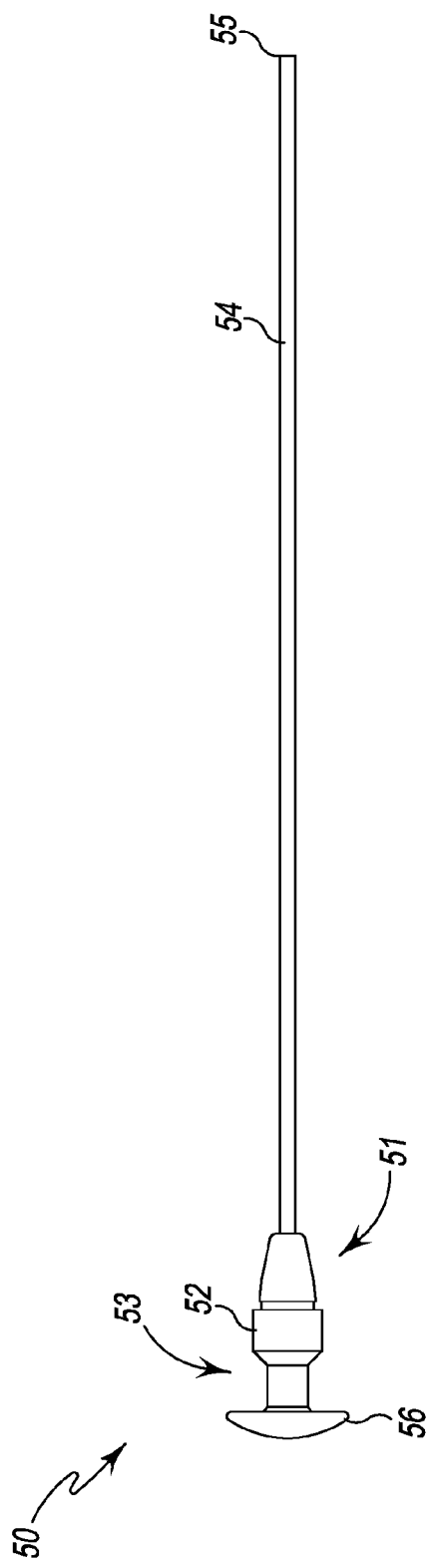

MEDICAL INSTRUMENT SET AND METHOD OF USE FOR TREATING BONY ABERRATIONS OF THE CALCANEUS

CROSS-REFERENCE TO RELATED APPLICATIONS

This U.S. non-provisional patent application claims the benefit of and/or priority under 35 U.S.C. § 119(e) to U.S. provisional patent application Ser. No. 62/213,364 filed Sep. 2, 2015 titled "Medical Instrument Set and Method of Use for Treating Bony Aberrations of the Calcaneus," the entire contents of which is specifically incorporated herein by reference.

FIELD OF THE INVENTION

The present invention relates to medical instruments and methods of use and, particularly, to medical instruments and methods of use for treating bony aberrations of the calcaneus such as calcaneal compression fractures.

BACKGROUND

The foot has many bones of various sizes, shapes and function. A main bone of the foot is the heel bone or calcaneus. The calcaneus is a large tarsal bone that articulates anteriorly with the cuboid bone and superiorly with the talus bone. The calcaneus transmits the majority of body's weight from the talus bone to the ground. Because of this, the calcaneus may experience bony aberrations such as fractures and/or other types of conditions due to various reasons.

Calcaneal fractures are often attributed to shearing stress adjoined with compressive forces combined with a rotary direction. These forces are typically linked to injuries in which an individual falls from a height, is involved in an automobile accident, or undergoes muscular stress where the resulting forces can lead to fracture. Calcaneal fractures can also be the result of problems associated with osteoporosis and/or diabetes.

No matter the cause, calcaneal fractures causes pain over the heel area. Other symptoms include the inability to bear weight over the involved foot, limited mobility of the foot, and limping. The area typically includes swelling, redness, and hematomas. The heel may also become widened with associated edema due to displacement of lateral calcaneal border.

Treatment may be non-surgical or surgical depending on the particular case. A closed reduction with or without fixation, or fixation without reduction are two non-surgical treatments. If surgical treatment is indicated, a conservative treatment is a closed reduction with percutaneous fixation. This approach however, has its pros and cons. Pros include less wound complications, better soft tissue healing, and decreased intraoperative time. Cons include an increased risk of inadequate calcaneal bone fixation compared to open reduction treatments. This can cause future consequences for the patient. Therefore, open reduction with internal fixation (ORIF) is generally the preferred surgical treatment, particularly for displaced intrarticular fractures. Nonetheless, as with any open surgical procedure, there are associated risks.

In view of the above, it is apparent that improvements can be made in the surgical treatment of bony aberrations, particularly in medical instruments and their method of use for treating bony aberrations of the calcaneus such as calcaneal compression fractures. As such, it is desirable to have a better surgical treatment for bony aberrations of the calcaneus such as, but not limited to, calcaneal compression fractures that overcomes the deficiencies of the prior art. It is therefore desirable to have medical instruments and methods of their use for surgically treating bony aberrations of the calcaneus such as, but not limited to, calcaneal compression fractures.

SUMMARY OF THE INVENTION

The present invention achieves the above-stated desires by providing a medical instrument set and method of use for surgically treating bony aberrations of the calcaneus such as, but not limited to, calcaneal compression fractures. The present medical instrument set allows surgical treatment of bony aberrations through a minimally invasive procedure. The minimally invasive procedure provides better outcomes than both a closed reduction and an open reduction.

The medical instrument set includes one or more of an access needle, a drill, a depth guide, a cement plunger, and a curette.

The access needle, or trocar, is used to provide access to a desired calcaneal site and is characterized by a cannula and a removable trocar tip. The cannula provides a hollow (cannulated) shaft that is open at both a distal end and a proximal end thereof and is sized to receive the trocar tip and allow a sharpened end of the trocar tip to extend beyond the distal end of the cannula. A handle is situated about the proximal end of the hollow shaft and provides access to the hollow shaft via the open proximal end of the hollow shaft. The handle is preferably, but not necessarily, ergonomically configured for easy manipulation by the user.

The trocar tip includes a seal for the hollow of the shaft of the cannula in the form of a cap that is situated on a proximal end of an elongated rod whose distal end comprises the sharpened blade. The elongated rod of the trocar tip has an outer diameter that is slightly less than inner diameter of the shaft hollow of the cannula and a length to at least extend to the open distal end of the hollow shaft of the cannula.

Structure of the cap cooperates with a cap reception structure of the handle to removably retain the cap on the handle. This retains the elongated rod within the hollow shaft of the cannula, the sharpened end extending beyond the hollow shaft of the cannula, and the hollow shaft of the cannula sealed at its proximal end. The removable trocar tip provides controlled access to the open proximal end and thus the hollow of the shaft such that an item or items may be inserted into and through the hollow shaft of the cannula when the trocar tip is removed. In an exemplary form, the cap reception structure includes a slot that accepts a flange structure of the cap.

The drill is used to bore into the calcaneus and is characterized by a preferably, but not necessarily, solid shaft having bone drill threading on a distal end of the shaft, and a handle on a proximal end of the shaft. The shaft has a working length sufficient to allow the distal bone drill threading of the shaft to extend beyond the distal end of the cannula of the access needle. The bone drill threading or drill length at the distal end of the drill shaft is adequate to penetrate a desired depth into the calcaneus.

The depth guide is used to visually indicate how far a medical instrument, portion or shaft thereof, extends through the access needle cannula and/or beyond the distal end of the access needle cannula and is characterized by a generally cylindrical body with a head at one end and an elongated portion extending from the head, the elongated portion having a smaller diameter than the head. A bore extends through the body from the head through the elongated portion.

A fitting is connected to a marker that is disposed in the elongated portion with the elongated portion having demarcations that show depth of an instrument that extends through the depth guide. The fitting is on the head opposite the elongated portion and is configured to receive the shaft of a medical instrument. As the fitting moves up and down, the marker correspondingly moves up and down. The fitting has a bore to receive the shaft of a medical instrument and to allow the shaft of the medical instrument to extend through the depth guide.

The cement plunger is used to introduce bone cement such as bone void filler (BVF) into the desired calcaneal site and is characterized by a cannulated shaft having an open distal end and an open proximal end with a handle disposed at the proximal end. The handle incorporates a Luer Lock or the like at the open proximal end that removably receives a cap and a syringe, the syringe having bone cement (e.g. BVF) for injection through the cannulated shaft of the cement plunger and into a void and/or fracture at the desired calcaneal site.

The curette is used to mechanically create a void at the desired calcaneal site and is characterized by a solid shaft having a distal end with a blade, and a proximal end with a handle. The shaft has a working length sufficient to allow the distal blade of the shaft to extend beyond the distal end of the access needle cannula. The blade is preferably, but not necessarily, curved or bent relative to the shaft and includes a configured tip for creating a void in the calcaneus. The blade has a length sufficient to reach the desired calcaneal site and create the desired calcaneal void.

Treatment of bony aberrations of the calcaneus using the present medical instrument set provides a minimally invasive approach. A plugged (via the trocar tip) access needle is placed into the calcaneus via a stab incision or a simple puncturing the plugged access needle through the skin and into the bone. With the use of fluoroscopy or a die marker, a physician can locate the bone fracture, void or edema with the tip of the inserted plugged access needle. This may be accomplished by hand insertion or with the use of a mallet. In one manner, once the location is identified, the trocar tip of the access needle is removed and a k-wire is inserted into the lumen (access needle shaft or cannula) to preserve the location. After k-wire insertion, the cannula/shaft of the access needle is removed and then a larger cannula is inserted over the k-wire. Through the larger cannula, a mechanical bone creator (curette) is fed into the desired calcaneal site. In another manner, the curette is designed to fit within the cannula of the access needle. Through mechanical (e.g. hand) manipulation, the blade of the curette creates a small fenestra or void at the distal end of the cannula for reception of bone cement (e.g. BVF) in order to augment and stabilize the fracture. The curette is removed after the void has been created in order to fill the distal void with the BVF. A syringe of BVF attaches to the proximal end of the cannula preferably, but not necessarily, via a Luer Lock or the like. The BVF is injected into the calcaneal site to stabilize the fracture.

It should be noted that the same cannula mechanism may be used to inject BVF into the central lumen of a fracture screw in the same location. In some instances, the surgeon will install a screw across the fracture line of a calcaneal break. The cannula is configured to be inserted into the screw to allow for BVF to be injected into the fracture site via the cannula and fracture screw.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate a form of the present invention, wherein:

FIG. 1 is a plan view of a curette of the present medical instrument set for treating bony aberrations of the calcaneus;

FIG. 2 is a side view of the curette of FIG. 1;

FIG. 5 is a plan view of a drill of the present medical instrument set for treating bony aberrations of the calcaneus;

FIG. 6 is a side view of the drill of FIG. 5;

FIG. 7 is a plan view of an access needle of the present medical instrument set for treating bony aberrations of the calcaneus;

FIG. 8 is a side view of the access needle of FIG. 7;

FIG. 9 is a plan view of a cement plunger of the present medical instrument set for treating bony aberrations of the calcaneus;

FIG. 10 is a side view of the cement plunger of FIG. 9;

DETAILED DESCRIPTION OF THE INVENTION

Figure 8A:
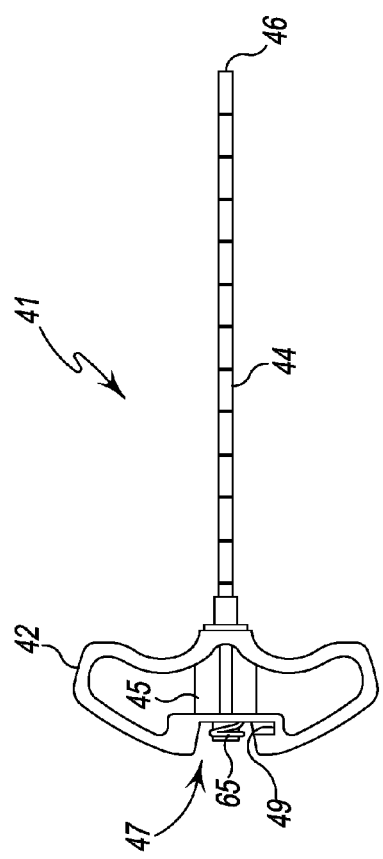
FIG. 8A is a side view of a cannula portion of the access needle of FIGS. 7 and 8.
Figure 8B:
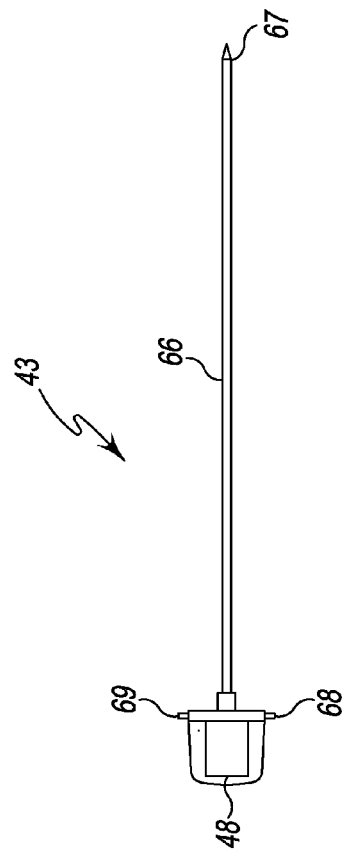
FIG. 8B is a side view of a trocar tip portion of the access needle of FIGS. 7 and 8.

Referring to FIGS. 1 and 2, there is depicted an exemplary form of a curette generally designated 10, fashioned in accordance with the present principles and being one medical instrument of a set of medical instruments for treating bony aberrations of the calcaneus such as, but not limited to, calcaneal compression fractures. The curette has a handle 12 with a shaft 14 extending from the handle 12 such that the handle 12 is situated at a proximal end of the shaft 14. A blade 16 is situated at a distal end of the shaft 14. As best seen in FIG. 2, the blade 16 is defined by curved portion 17 that extends from the distal end of the shaft 14 with a scoop 18 at the end of an angled portion 17. The shaft 14 has a working length (e.g. 23.8 cm) sufficient to allow the blade 16 to extend beyond the distal end of the access needle shaft when the curette is inserted into an access needle (see access needle 40 of FIGS. 7-8). The blade has a blade length (e.g. 20 mm) adequate to reach and create a void at the desired calcaneal site.

Figure 3:
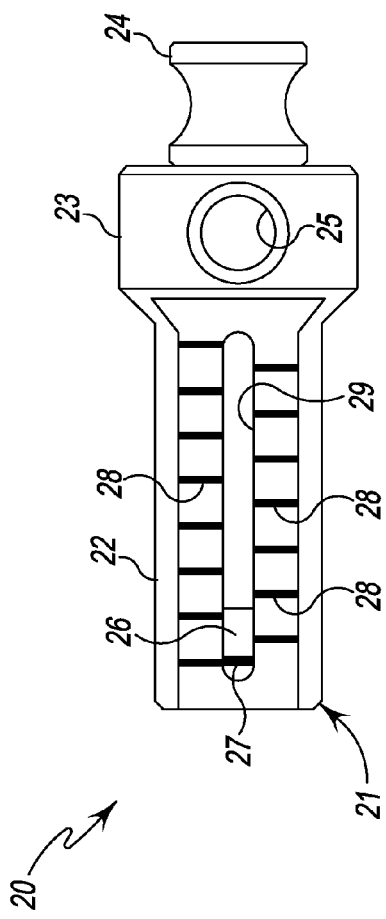
FIG. 3 is a side view of a depth guide of the present medical instrument set for treating bony aberrations of the calcaneus.
Figure 4:
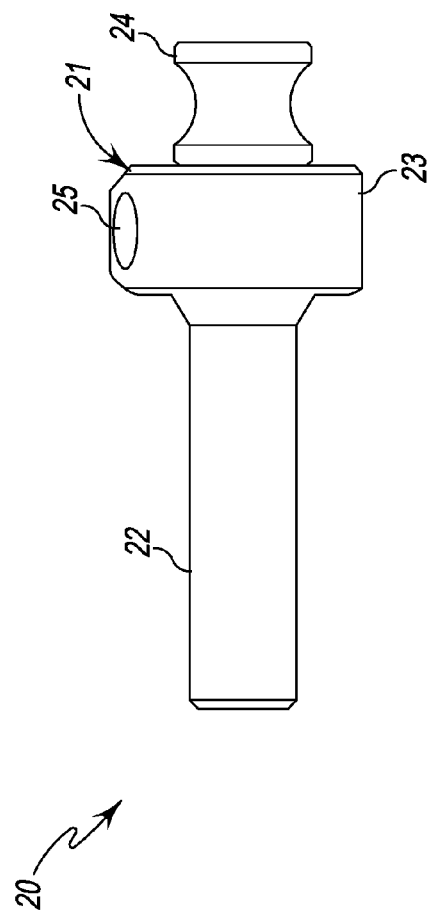
FIG. 4 is another side view of the depth guide of FIG. 3.

Referring to FIGS. 3 and 4, there is depicted an exemplary form of a depth guide, generally designated 20, fashioned in accordance with the present principles and being one medical instrument of a set of medical instruments for treating bony aberrations of the calcaneus such as, but not limited to, calcaneal compression fractures. The depth guide 20 has a generally cylindrical body 21 with a head 23 at one end and an elongated portion 22 extending from the head 23, the elongated portion 22 having a smaller diameter than the head 23. A bore (not seen) extends through the body 21 from the head 23 through the elongated portion 22. A fitting 24 is connected to a marker 26 that is disposed within a chamber 29 of the elongated portion 22. The fitting 24 has a bore (not shown) that receives an instrument shaft. A number of demarcations 28 are provided along the chamber 29 of the elongated portion 22 that show depth. As the fitting 24 moves with the instrument, the marker 26 and thus mark 27 moves along the chamber 29. A mark 27 shows depth relative to the demarcations 28. A button 25 is provided which upon compression allows for fitting 24 to translate. As fitting 24 elongates the curette tip exposure reduces when stacked upon the access cannula. The amount of tip exposure runs from 4 mm to 32 mm.

Referring to FIGS. 5 and 6, there is depicted an exemplary form of a drill, generally designated 30, fashioned in accordance with the present principles and being one medical instrument of a set of medical instruments for treating bony aberrations of the calcaneus such as, but not limited to, calcaneal compression fractures. The drill 30 has a handle 32 with a shaft 34 extending from the handle 32 such that the handle 32 is situated at a proximal end of the shaft 34. Threads or threading 36 is situated at a distal end of the shaft 34. The shaft 34 has a working length (e.g. 21.9 cm) sufficient to allow the threading 36 to extend beyond the distal end of the access needle shaft when the drill is inserted into the access needle 40 (see FIGS. 7-8). The length of threading 36 defines a drill length. The drill length (e.g. 38 mm) is adequate to reach a desired calcaneal site.

Referring to FIGS. 7, 8, 8A, and 8B, there is depicted an exemplary form of an access needle, generally designated 40, fashioned in accordance with the present principles and being one medical instrument of a set of medical instruments for treating bony aberrations of the calcaneus such as, but not limited to, calcaneal compression fractures. The access needle 40 is characterized by a cannula portion (cannula) 41 (see FIG. 8A) and a trocar tip portion (trocar tip) 43 (see FIG. 8B). The cannula portion 41 includes a handle 42 having a central body 45 with a hollow shaft 44 extending from the body 45 such that the handle 42 is situated about an open proximal end of the hollow shaft 44. A boss 65, situated on an end of the body 45, is in communication with the open proximal end of the hollow shaft 44, and is configured to releasably receive a cap 48 of the trocar tip 40 (see FIG. 8B and below). The distal end of the hollow shaft 44 terminates in an open end 46. The hollow shaft 44 is thus open from its distal end 46 to its proximal end 65. The shaft 44 has a working length (e.g. 12.9 cm) sufficient to allow the other medical instruments to extend beyond the end 46 when inserted into the hollow shaft 44. The handle 42 is preferably, but not necessarily, ergonomically configured for easy manipulation by the user.

The trocar tip 43 includes a seal for the open proximal end of the hollow shaft 44 of the cannula 41 in the form of a cap 48 that is configured to releasably join with the boss 65 of the handle 42 such that the proximal opening of the hollow shaft 44 of the cannula 41 is obturated. An elongated rod 66 extends from the cap 48 and terminates at its distal end in a pointed blade 67. The pointed blade 67 is preferably, but not necessarily, cut at an angle or bias. Other sharp and/or pointed style tips may be used. The rod 66 is sized such that it is slightly less than the inner diameter of the shaft hollow 44 with a length to at least extend to the open distal end 46 of the hollow shaft 44 such that the blade 67 is beyond the open distal end 46.

When the cap 48 is releasably held over and/or onto the boss 65 of the handle 42, the rod 66 extends through the hollow shaft 44 and the blade 67 is exposed, thereby releasably retaining the trocar tip 43 in the cannula 41. Structure in the form of a flange 68 of the cap 48 cooperates with a cap reception structure 47 of the handle 42 to removably retain the cap 48 on the handle 42, and thus the rod 66 within the hollow shaft 44. The removable trocar 43 provides controlled access to the hollow shaft 44 such that an item or items may be inserted into and through the hollow shaft 44 when the trocar 43 is removed. In an exemplary form, the cap reception structure 47 of the handle 42 includes a slot 49 that accepts the flange structure 68 of the cap 48.

Referring to FIGS. 9 and 10, there is depicted an exemplary form of a cement plunger, generally designated 50, fashioned in accordance with the present principles and being one medical instrument of a set of medical instruments for treating bony aberrations of the calcaneus such as, but not limited to, calcaneal compression fractures. The cement plunger 50 has a handle 52 with a hollow shaft 54 extending from the handle 52 such that the handle 52 is situated at a proximal end of the shaft 54. The distal end of the shaft 54 terminates in blunt tip 55. The hollow shaft 54 thus has an opening at its distal end and an opening at its proximal end. The shaft 54 has a working length (e.g. 21.9 cm) sufficient to extend through and beyond the distal tip 46 of the hollow shaft 44 of the cannula 41 of the access needle 40. The handle 52 includes a closure structure 53 formed as a cap 56 that removably couples with mating structure (not seen) on an end 57 of the handle 52, the end 57 providing access to the hollow shaft 54 from its proximal end. The mating structure may be a Luer Lock or the like. Once the cap 56 is removed, a syringe (not shown) having a mating Luer Lock (structure) is received on the end 57, the syringe having BVF or other bone cement.

Figure 11:
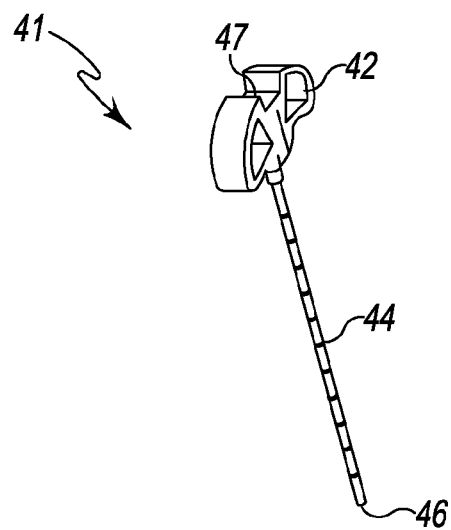
FIG. 11 is a first view of several views of one or more of the various medical instruments of the present medical instrument set for treating bony aberrations of the calcaneus illustrating a procedure for treating calcaneal compression fractures, the first view showing a positioned cannula of the access needle (i.e. the trocar tip having been removed from the cannula of the access needle)
Figure 12:
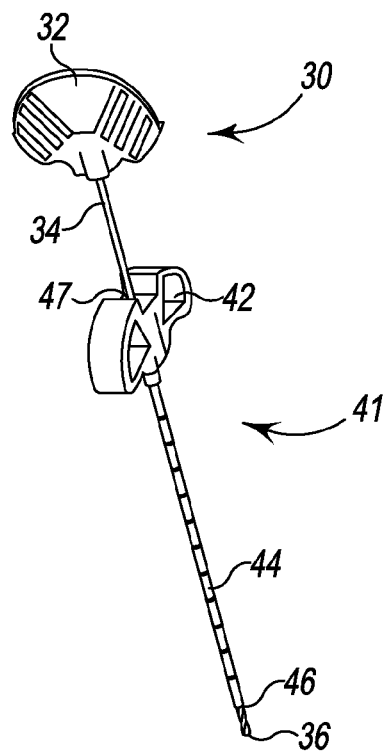
FIG. 12 is a second view of the several views of one or more of the various medical instruments of the present medical instrument set for treating bony aberrations of the calcaneus illustrating the procedure for treating calcaneal compression fractures, the second view depicting the cannula of the access needle of FIG. 11 with the drill inserted through the hollow shaft of the cannula of the access needle.

FIGS. 11-14 depict several of the present medical instruments as used in the present method for treating bony aberrations of the calcaneus and, for this particular illustration, a method of treating a calcaneal compression fracture that provides a minimally invasive approach. FIG. 11 shows the cannula 41 of the access needle 40 with the trocar tip 43 of the access needle 40 has been removed after the access needle 40 was placed into the calcaneus (not shown) via a stab incision or a simple puncturing the plugged access needle 40 through the skin and into the bone. With the use of fluoroscopy, die marker or otherwise, a surgeon locates the bone fracture with the blade 67 of the trocar tip 43 of the access needle 40. This may be accomplished by hand insertion, with the use of a mallet, or otherwise. In FIG. 12, the drill 30 is shown inserted into the cannula 41 with its bone drill threading 36 extending beyond the tip 46 of the cannula shaft 44. The drill 30 may then be used to reach a desired location within the calcaneus through hand manipulation (i.e. twisting) of the handle 32 of the drill 30.

Figure 13:
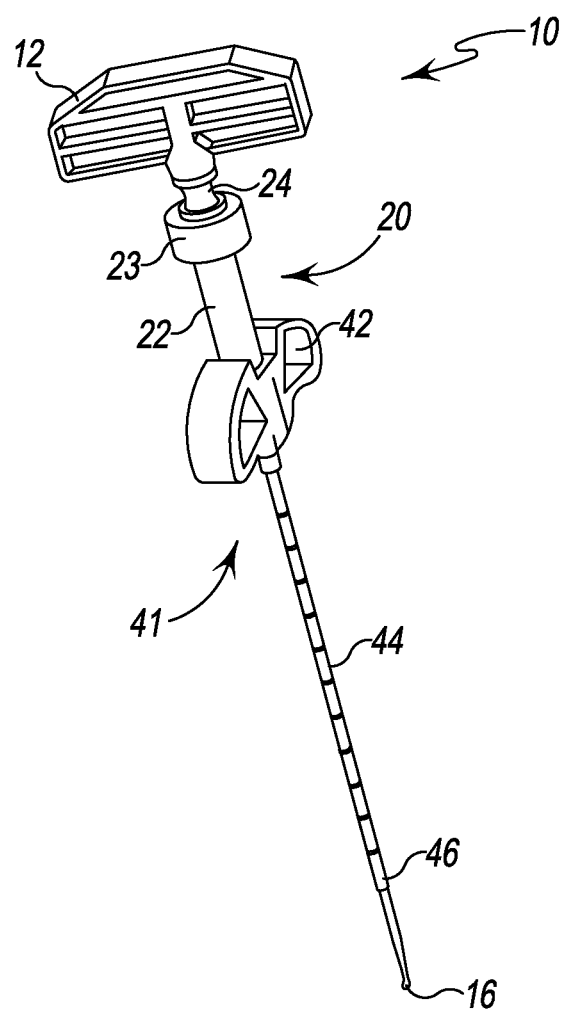
FIG. 13 is a third view of the several views of one or more of the various medical instruments of the present medical instrument set for treating bony aberrations of the calcaneus illustrating the procedure for treating calcaneal compression fractures, the third view depicting the depth guide received onto the handle of the cannula of the access needle, with the curette received in the depth guide and in the shaft of the cannula of the access needle.
Figure 14:
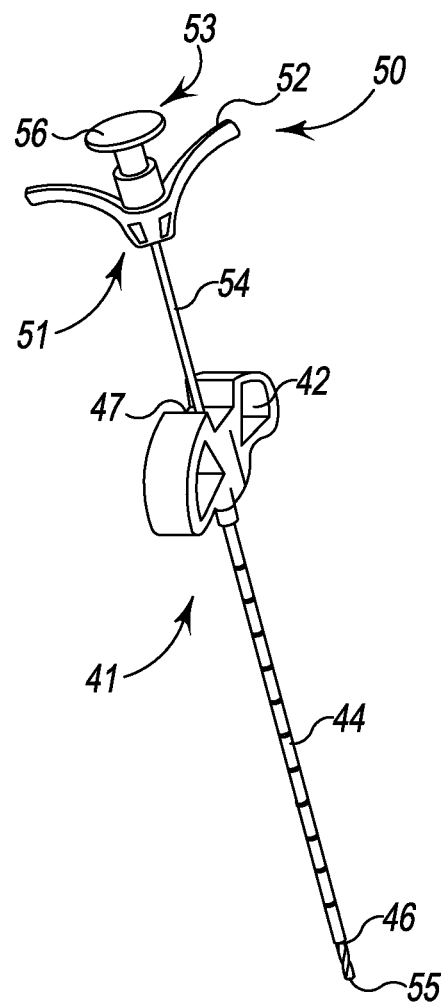
FIG. 14 is a fourth view of the several views of one or more of the various medical instruments of the present medical instrument set for treating bony aberrations of the calcaneus illustrating the procedure for treating calcaneal compression fractures, the fourth view depicting the cement plunger received in the shaft of the cannula of the access needle.

In FIG. 13, the drill guide 20 is shown coupled to the cannula 41 of the access needle 40 (particularly, the handle 42 thereof) with the curette 10 situated in the drill guide 20 and cannula 41. The curette 10 is situated in the drill guide 20 such that the handle 12 of the curette 10 abuts the fitting 24. The curette 10 is shown at a maximum depth relative to the cannula 41 such that the blade 16 extends a maximum distance beyond the tip 46 of the cannula 41. The mark 27 of the marker 26 of the depth guide will be at its lowest point within the indicator 29 thus indicating a maximum depth. Upward and downward movement of the fitting 24 of the depth guide 20 moves the position of the curette up and down relative to the cannula 41 thus setting a depth of the blade 16 of the curette 10 (or other of the present medical instruments), while correspondingly moving the mark 26 of the drill guide 20. Through mechanical (e.g. hand) manipulation, the blade 16 of the curette 10 creates a small fenestra or void at the distal end (tip 46) of the cannula 41 for reception of bone cement (e.g. BVF) in order to augment and stabilize the fracture. The curette 10 and the depth guide 20 are removed after the void has been created in order to fill the distal void (not shown) with the BVF. In FIG. 14, the cement plunger 50 is shown inserted into the cannula 41 in order to provide BVF to the distal void (not shown) of the calcaneus (not shown). The cap 56 is removed and a syringe of BVF attaches to handle 52 of the cement plunger 50 for injecting the BVF into the calcaneal site.

Figure 15:
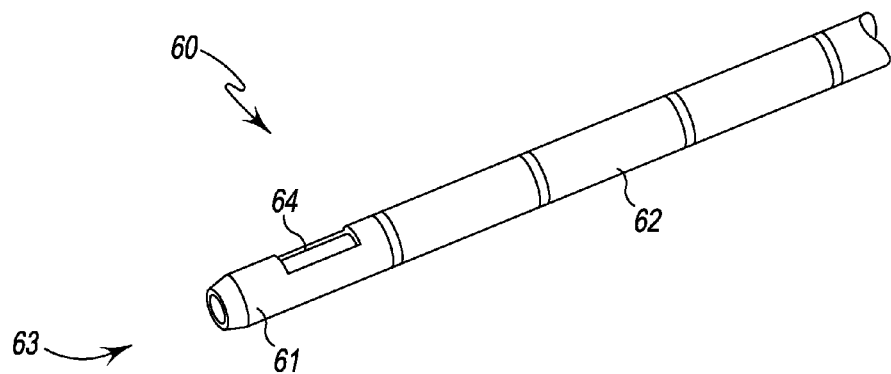
FIG. 15 is a partial view of a distal end of a notched cannula that may be part of one or more the present medical instruments, such as the access needle, or as a separate medical instrument of the present medical instrument set.

FIG. 15 depicts a cannula 60 as a medical instrument of the present set of medical instruments or as an augmentation of one of the present medical instruments such as the cannula 41 of the access needle 40. The cannula 60 is defined by longitudinal shaft 62 having an internal, longitudinal bore 63 extending from a proximal end (not shown) thereof to the distal end 61 thereof. A fenestra or opening 64, which may be one of several, is disposed in the side of the shaft 62 proximate the distal end 61 thereof. This cannula can be used to inject BVF into the central lumen of a bone fracture screw (such as bone fracture screw 70 shown in FIGS. 16 and 17, and described in greater detail below) in the same desired calcaneal site. In some instances, the surgeon will install a bone fracture screw across the fracture line of a calcaneal break. The cannula is thus designed to be inserted into the bone fracture screw 70 (see FIG. 16) to allow for BVF to be injected into the fracture site, via the cannula 60 and bone fracture screw 70.

Figure 16:
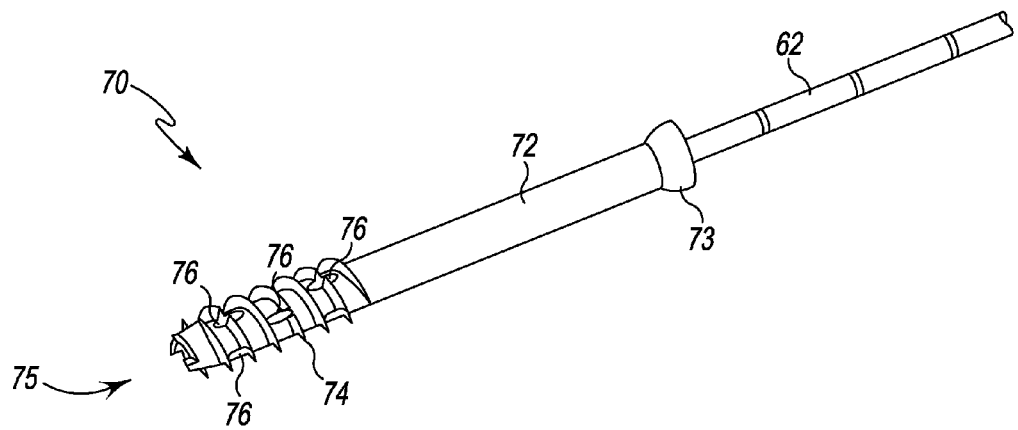
FIG. 16 is a view of a cannulated and fenestrated bone screw of the present medical instrument set with the notched cannula received in the cannula of the bone screw.
Figure 17:
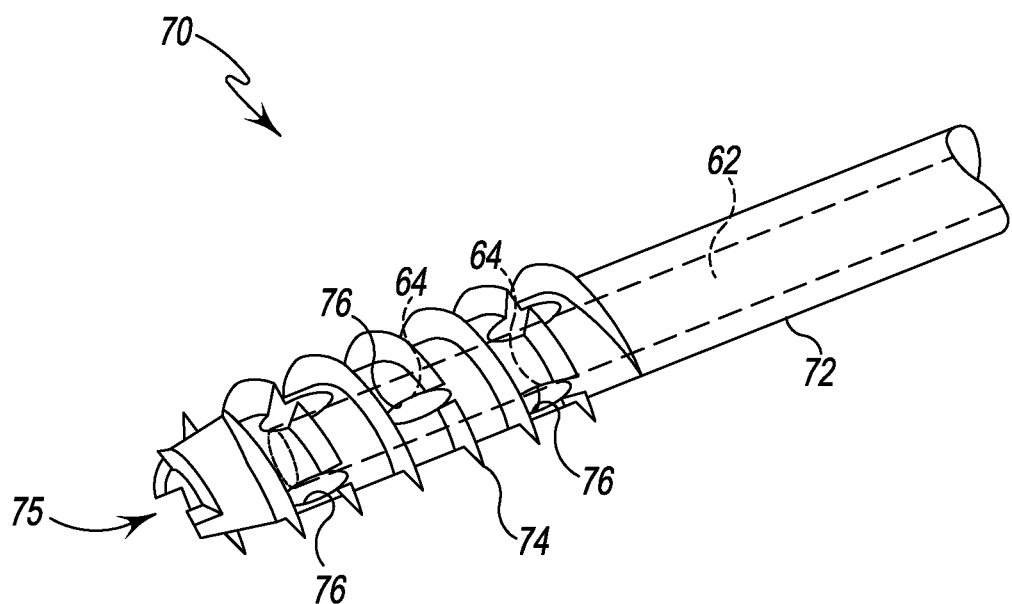
FIG. 17 is an enlarged view of the distal end of the bone screw of FIG. 16.

Referring to FIGS. 16 and 17, there is depicted an exemplary form of a bone fracture screw, generally designated 70, fashioned in accordance with the present principles and being one medical instrument of a set of medical instruments for treating bony aberrations of the calcaneus such as, but not limited to, calcaneal compression fractures. The bone fracture screw 70 has a shaft 72 having a head 73 at a proximal end of the shaft 72, and bone screw threading 74 at a distal end of the shaft 72. A longitudinal bore 75 extends through the shaft 72 from the proximal end to the distal end. The bone fracture screw 70 includes several fenestrae 76 situated about the bone screw threading 74 at the distal end of the shaft 72. The fenestrae 64 of the cannula 60 may be aligned with the fenestrae 76 of the fracture screw 70.

It should be appreciated that many medical instrument sets may be formed using permutations of the various medical instruments described herein.

It should also be appreciated that dimensions of the medical instruments of the present medical instrument set's components, structures, and/or features can be altered as desired.

What is claimed is:

1. A method of treating bony aberrations of the calcaneus comprising the steps of:
   providing a set of medical instruments for treating bony aberrations of the calcaneus, the set of medical instruments comprising:
   a cannula;
   a trocar;
   a drill;
   a depth guide;
   a cement plunger; and
   a curette;
   using the cannula and trocar to reach a bony aberration;
   using the drill with the cannula to prepare the bony aberration;
   using the curette and depth guide with the cannula to remove material relating to the bony aberration to create a void; and
   using the cement plunger with the cannula to implant cement into the void.

2. The method of claim 1, wherein the cannula comprises:
   an ergonomic handle having a center section with a bore extending from a first end of the center section to a second end of the center section;
   a tube extending from the second end of the ergonomic handle and in communication with the bore; and
   an externally threaded boss at the first end of the ergonomic handle and in communication with the bore.

3. The method of claim 2, wherein the trocar comprises:
   an elongated needle having a first end and a second end;
   a trocar tip at the second end of the elongated needle; and
   a knob at the first end of the elongated needle, the knob having internal threading that corresponds with the external threading of the boss.

4. The method of claim 1, wherein the drill comprises:
   a handle;
   an elongated rod having a first end in the handle, and a second end distal the handle, the elongated rod defining a working length; and
   drill threading at the second end of the elongated rod, the drill threading defining a drill length.

5. The method of claim 4, wherein the drill length is congruent with the working length.

6. The method of claim 1, wherein the depth guide comprises:
a first generally tubular body having a distal end and a proximal end and a bore extending from the distal end to the proximal end, a head disposed at the proximal end of the first generally tubular body, and an elongated opening disposed along a portion of the first generally tubular body, the elongated opening providing communication with the bore; and
a second generally tubular body having a distal portion and a proximal portion, and a bore extending from the distal portion to the proximal portion, a nub on the proximal portion and providing a stop against the head of the first generally tubular body, the distal portion extending into the bore of the first generally tubular body so as to be visible from exterior of the first generally tubular body via the elongated opening of the first generally tubular body.

7. The method of claim 6, wherein a marker is provided on the distal portion extending into the bore of the first generally tubular body, the marker providing a visual demarcation.

8. The method of claim 1, wherein the cement plunger comprises:
a first handle;
a hollow rod extending from the first handle, the hollow rod having a first end situated in the first handle, and a second end distal the first handle, access to the hollow of the rod via the first handle;
a second handle; and
a solid rod extending from the second handle and having an end distal to the second handle that is adapted to eject cement from the hollow rod.

9. The method of claim 8, wherein the second handle is configured as a knob.

10. The method of claim 1, wherein the curette comprises:
a handle;
a rod extending from the handle and having an end distal to the handle; and
a blade disposed on the end distal to the handle.

11. The method of claim 10, wherein the blade is curved from the end distal to the handle.

12. The method of claim 11, wherein the rod and blade define a working length.

13. The method of claim 1, wherein the step of providing a set of medical instruments for treating bony aberrations of the calcaneus comprises using a set of medical instruments comprising:
a cannula, the cannula having:
an ergonomic handle with a center section with a bore extending from a first end of the center section to a second end of the center section;
a tube extending from the second end of the ergonomic handle and in communication with the bore; and
an externally threaded boss at the first end of the ergonomic handle and in communication with the bore;
a trocar, the trocar having:
an elongated needle having a first end and a second end;
a trocar tip at the second end of the elongated needle; and
a knob at the first end of the elongated needle, the knob having internal threading that corresponds with the external threading of the boss;
a drill, the drill having:
a handle;
an elongated rod having a first end in the handle, and a second end distal the handle, the elongated rod defining a working length; and
drill threading at the second end of the elongated rod, the drill threading defining a drill length;
a depth guide, the depth guide having:
a first generally tubular body having a distal end and a proximal end and a bore extending from the distal end to the proximal end, a head disposed at the proximal end of the first generally tubular body, and an elongated opening disposed along a portion of the first generally tubular body, the elongated opening providing communication with the bore; and
a second generally tubular body having a distal portion and a proximal portion, and a bore extending from the distal portion to the proximal portion, a nub on the proximal portion and providing a stop against the head of the first generally tubular body, the distal portion extending into the bore of the first generally tubular body so as to be visible from exterior of the first generally tubular body via the elongated opening of the first generally tubular body;
a cement plunger, the cement plunger having:
a first handle;
a hollow rod extending from the first handle, the hollow rod having a first end situated in the first handle, and a second end distal the first handle, access to the hollow of the rod via the first handle;
a second handle; and
a solid rod extending from the second handle and having an end distal to the second handle that is adapted to eject cement from the hollow rod; and
a curette, the curette having:
a handle;
a rod extending from the handle and having an end distal to the handle; and
a blade disposed on the end distal to the handle.

14. The method of claim 13, wherein the drill length is congruent with the working length.

15. The method of claim 13, wherein a marker is provided on the distal portion extending into the bore of the first generally tubular body, the marker providing a visual demarcation.

16. The method of claim 13, wherein the second handle is configured as a knob.

17. The method of claim 13, wherein the blade is curved from the end distal to the handle.

18. The method of claim 17, wherein the rod and blade define a working length.

* * * * *